(12) United States Patent
Moskal et al.

(10) Patent No.: US 10,740,436 B2
(45) Date of Patent: Aug. 11, 2020

(54) DATA SET DISTRIBUTION DURING MEDICAL DEVICE OPERATION

(71) Applicant: Fenwal, Inc., Lake Zurich, IL (US)

(72) Inventors: Witold Moskal, Lake Zurich, IL (US); Maciej Wroblewski, Lake Zurich, IL (US)

(73) Assignee: FENWAL, INC., Lake Zurich, IL (US)

( * ) Notice: Subject to any disclaimer, the term of this patent is extended or adjusted under 35 U.S.C. 154(b) by 254 days.

(21) Appl. No.: 15/359,680

(22) Filed: Nov. 23, 2016

(65) Prior Publication Data

US 2017/0147761 A1    May 25, 2017

Related U.S. Application Data

(60) Provisional application No. 62/659,942, filed on Nov. 25, 2015.

(51) Int. Cl.
*A61M 5/172*    (2006.01)
*A61M 5/142*    (2006.01)
(Continued)

(52) U.S. Cl.
CPC .......... *G06F 19/326* (2013.01); *A61M 5/142* (2013.01); *A61M 5/172* (2013.01); *G06F 19/3456* (2013.01); *G06F 19/3468* (2013.01); *G16H 70/40* (2018.01); *G16H 70/60* (2018.01); *A61M 2205/3584* (2013.01); *A61M 2205/502* (2013.01); *A61M 2205/60* (2013.01)

(58) Field of Classification Search
CPC ...... G06F 15/177; G06F 9/44; G06F 19/3412; G06F 19/00; G06F 19/326; G06F 3/048; A61M 5/172; A61M 5/142

USPC ...................................... 705/2; 717/171, 173
See application file for complete search history.

(56) References Cited

U.S. PATENT DOCUMENTS 8,768,719 B2 *    7/2014    Wehba ................. A61M 5/142
                                                                    705/2
9,089,642 B2 *    7/2015    Murphy ................. A61M 5/00
(Continued)

OTHER PUBLICATIONS

European Patent Office, "Extended European Search Report", issued in connection with European patent application No. 16002493.1, dated Apr. 11, 2017, 8 pages.
(Continued)

*Primary Examiner* — Aryan E Weisenfeld
*Assistant Examiner* — Alaaeldin M Elshaer
(74) *Attorney, Agent, or Firm* — Hanley, Flight & Zimmerman, LLC

(57) ABSTRACT

Certain examples provide systems, methods, and apparatus for medical device management. An example method includes comparing a first identification of a first data set to a second identification of a second data set at a medical device. The example method includes, when the first identification does not match the second identification, triggering a download of the second data set to the medical device. The example method includes determining an operating state of the medical device. The example method includes, when the operating state indicates the medical device is idle, triggering activation of the second data set in place of the first data set at the medical device. The example method includes facilitating operation of the medical device according to the second data set.

20 Claims, 18 Drawing Sheets

(51) Int. Cl.
  *G06F 19/00* (2018.01)
  *G16H 70/40* (2018.01)
  *G16H 70/60* (2018.01)

(56) References Cited

U.S. PATENT DOCUMENTS

| | | | | |
|---|---|---|---|---|
| 9,307,907 | B2* | 4/2016 | Condurso | G06F 19/326 |
| 9,539,383 | B2* | 1/2017 | Kohlbrecher | A61M 5/142 |
| 10,042,986 | B2* | 8/2018 | Ruchti | G06F 19/3468 |
| 10,061,899 | B2* | 8/2018 | Miller | A61M 1/288 |
| 2004/0167465 | A1 | 8/2004 | Mihai et al. | |
| 2004/0176984 | A1* | 9/2004 | White | A61M 5/142 |
| | | | | 705/2 |
| 2007/0168223 | A1* | 7/2007 | Fors | G06F 19/324 |
| | | | | 705/2 |
| 2008/0059237 | A1 | 3/2008 | Koren et al. | |
| 2008/0154177 | A1* | 6/2008 | Moubayed | G06F 19/3468 |
| | | | | 604/19 |
| 2009/0094682 | A1 | 4/2009 | Sage et al. | |
| 2009/0270810 | A1 | 10/2009 | DeBelser et al. | |
| 2011/0047499 | A1* | 2/2011 | Mandro | A61M 5/142 |
| | | | | 715/780 |
| 2011/0289497 | A1* | 11/2011 | Kiaie | G06F 8/65 |
| | | | | 717/171 |
| 2013/0104120 | A1* | 4/2013 | Arrizza | G06F 8/65 |
| | | | | 717/173 |
| 2013/0110538 | A1* | 5/2013 | Butterfield | G16H 40/63 |
| | | | | 705/2 |
| 2013/0312066 | A1* | 11/2013 | Suarez | G06F 19/3418 |
| | | | | 726/4 |
| 2014/0095180 | A1* | 4/2014 | Venkat | G06Q 50/22 |
| | | | | 705/2 |
| 2014/0194817 | A1 | 7/2014 | Lee et al. | |
| 2014/0304773 | A1 | 10/2014 | Woods et al. | |
| 2015/0141955 | A1* | 5/2015 | Ruchti | G16H 20/17 |
| | | | | 604/506 |
| 2015/0370973 | A1* | 12/2015 | Jones | G06F 19/326 |
| | | | | 705/2 |
| 2016/0034655 | A1* | 2/2016 | Gray | G06F 19/3468 |
| | | | | 713/1 |

OTHER PUBLICATIONS

European Patent Office, "Extended European Search Report", issued in connection with European patent application No. 16002492.3, dated Apr. 12, 2017, 9 pages.
United States Patent and Trademark Office, "Non-Final Office Action," dated May 31, 2019 in connection with U.S. Appl. No. 15/359,690 (16 pages).
Dean Wiech, "Role based acess control in Healthcare," Aug. 26, 2013, Healthcare IT News, 15 pages.
Jasmine Pennic, "Role-Based Access Control Ensures Extra Security in Healthcare," May 7, 2013, hitconsultant.net, 11 pages.
Frode Hansen and Vladimir Oleshchuk, "Application of Role-Based Access Control in Wireless Healthcare Information Systems," Mar. 2004, Agder University College, 5 pages.
United States Patent and Trademark Office, "Non-Final Office action," issued in connection with U.S. Appl. No. 15/359,690, dated Dec. 10, 2018, 26 pages.
Science Applications International Corporation (SAIC), Role-Based Access Control (RBAC) Role Engineering Process, Version 3.0, The Healthcare RBAC Task Force, May 11, 2004, 40 pages.
Elisa Bertin et al., GEO-RBAC: A Spatially Aware RBAC, ACM Transactions on Information and System Security, Jan. 2005, 40 pages.
Indrakshi Ray et al., LRBAC: A location-aware role-based access control model, Information System Security, Dec. 2006, 16 pages.
Edward Killeen, Role mapping for complete RBAC, empowerID, Sep. 11, 2012, 4 pages.
European Patent Application, "Communication pursuant to Article 94(3) EPC," issued in connection with European patent application No. 16 002 493.1, dated Nov. 2, 2018, 7 pages.
European Patent Application, "Communication pursuant to Article 94(3) EPC," issued in connection with European patent application No. 16 002 493.1, dated Oct. 10, 2019, 6 pages.
United States Patent and Trademark Office, "Non-Final Office Action," dated Jan. 31, 2020 in connection with U.S. Appl. No. 15/359,690 (13 pages).

* cited by examiner

FIG. 4E

DATA SETS > JIMDATASET-000 > CONFIRM POLICY CREATION

CONFIRM POLICY CREATION

PLEASE CONFIRM DISTRIBUTION OF DATA SET

WARNING THE CREATION OF THIS POLICY WILL OVERWRITE ONE OR MORE POLICIES

| DATA SET | JIMSDATASET-000 | |
|---|---|---|
| UPLOADED TIME | 10/9/2015 1:01 PM | |
| VIGILANT USER | PHARAMACIST | |
| APPLICABLE PRODUCT TYPE | AGLIA VP MC | |
| | AGLIA SP MC | |
| SELECTED PUMPS | | |
| HOSPITAL | | PUMP TOTAL |
| LAKE ZURICH | | 4 |
| DEVICE TYPE | | PUMP TOTAL |
| △AGILIA SP MC | | 2 |
| △AGILIA VP MC | | 2 |

CONFIRM     CANCEL

DATA SET DISTRIBUTION DURING MEDICAL DEVICE OPERATION

CROSS-REFERENCE TO RELATED APPLICATIONS

The present application relates and claims priority to U.S. Provisional Patent Application Ser. No. 62/259,942, filed on Nov. 25, 2015, which is herein incorporated by reference in its entirety for all purposes.

FIELD

The present disclosure relates generally to medical devices. More specifically, the present disclosure relates to methods, systems, and apparatus to facilitate data set distribution for medical devices.

BACKGROUND

Increasingly, medical devices are becoming electronic or involve an electronic or software component. Electronic devices, distributed facilities, and scattered patients make training, treatment, and troubleshooting difficult. Further, it is often difficult to educate the public, and patients may not seek the treatment they should due to a lack of information and access. Operators and administrators may also introduce inefficiencies in their operation and management of medical devices due to a lack of information and access. Additionally, unauthorized access and/or interruption has potential to introduce harmful error as well as inefficiency into patient treatment.

BRIEF DESCRIPTION OF SEVERAL VIEWS OF THE DRAWINGS

FIGS. 4A-4I depict example user interfaces for distribution policy creation.

Figure 1:
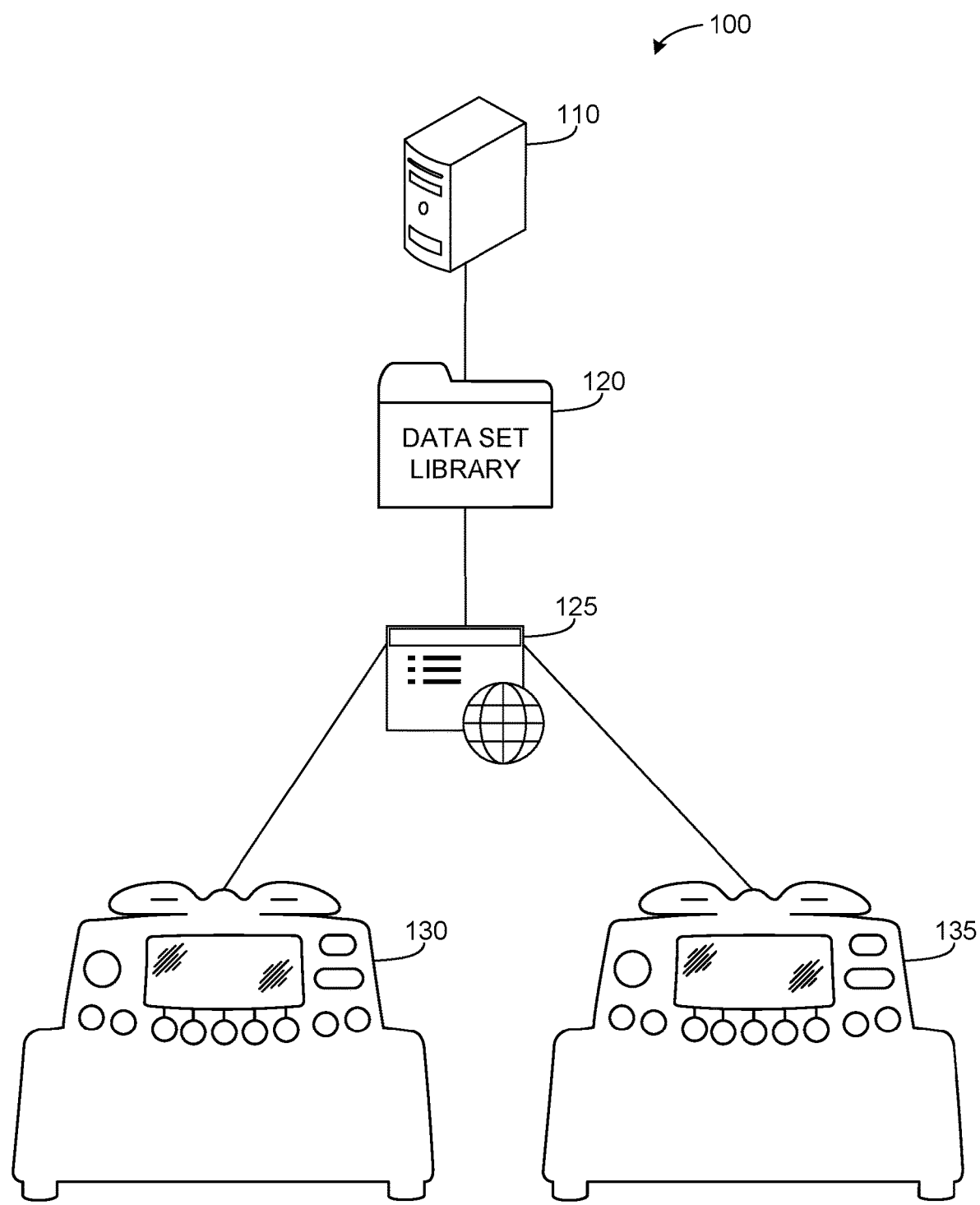
FIG. 1 illustrates an example medical device management system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

Certain examples facilitate management of medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) provides input regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

In certain examples, an operator or administrator may configure a medical device, such as an infusion pump, apheresis device, etc., and/or set one or more parameters for interaction between the device and a domain controller and/or a provider data management system. Certain examples provide flexibility in facilitating operator and/or administrator (e.g., user) operation and configuration of a medical device while maintaining device reliability and secure through new authorization protocols and systems.

Certain examples facilitate distribution of a data set to a medical device, such as an infusion pump, apheresis device, etc., while the medical device is in operation (e.g., during infusion of a patient via the infusion pump, etc.). Certain examples determine and/or update a data set distribution policy associated with a medical device data management system (such as the Fenwal DXT™ data management system manufactured by Fenwal™, a Fresenius Kabi company). If a data set distribution policy has been created, then a new or updated data set (e.g., a new or updated drug library) can be distributed to one or more medical devices, even if one or more of the target medical devices are currently operating (e.g., pump(s) are currently infusing drug into a patient). Thus, data set distribution does not impact the pump's activity.

Thus, a data management system can interact with medical devices (e.g., Fenwal Amicus™, Alyx™, Autopheresis-C™ and Aurora™ Apheresis systems, other apheresis devices, Fresenius Kabi Agilia® pump, Optima™ pump, Pilot™ pump, other drug delivery pump, etc.) for flexible, remote configuration and operation while helping to ensure data and configuration safety and security, for example. Data set distribution does not request that the medical device (e.g., infusion pump, apheresis device, etc.) stop mid-operation (e.g., stop infusion, stop collecting blood, etc.). Medical device operation and data set distribution can be performed simultaneously.

In certain examples, a data set defines a drug library and/or instruction set for a medical device such as a "smart" infusion pump, apheresis device, etc. For example, "smart" infusion pumps utilize a drug library or other close error reduction software to perform functions that assist healthcare providers with programming and calculating drug dose and delivery rates. The drug library is a database or data set that stores drug dosing information, including dosing limits, concentration, infusion parameters, and drug specific advisories, for example. Drug library instructions can help reduce or prevent medication errors and associated patient harm, for example.

In some examples, drug libraries let clinicians select medications and fluids from pre-loaded lists, which can be tailored to a healthcare facility, patient care area, etc. For example, a drug library profile used in an intensive care unit (ICU) may include vasoactive medications, but a drug library for a surgical unit may not include such medication. Some facilities also integrate smart infusion devices with electronic medical records, computerized order entry systems, and/or medication barcode scanning systems. Integrating these systems with smart pumps provides additional safety checks that may make administering medications safer. Healthcare facilities may choose to implement limitations, commonly called hard and soft limits (also referred to as dosing limits), on preselected drugs via the drug library. The limits set lower and upper bounds on dosage, infusion rate, etc., as defined by hospital, health system, clinic, etc.

Dosage and/or infusion rate bounds can be used to provide decision support to an operator, clinician, etc. If a clinician programs a smart pump outside predetermined dose or rate parameters for a drug with hard limits, the pump generates an alert and will not allow the clinician to proceed with the selection. Hard limits are typically set for high-risk drugs such as heparin. With soft limits, the clinician and/or other authorized user can override the alert and proceed with the infusion, for example. Infusion pumps and/or other devices can generate usage reports regarding how the pumps have been used, which drugs have been administered (e.g., type, frequency, dosage, total quantity, etc.), dose overrides, etc.

Distribution of a data set to medical devices can occur directly at the device and/or remotely over a network (e.g., from a data management system to multiple medical devices, etc.). However, wireless network distribution of new data set information to multiple medical devices has been an area of concern for administrators. Traditionally, drug library data set distribution is a lengthy process requiring devices to be turned on, idle, and connected to a network to receive a data set update. As a result, distributing a new data set wireless could previously take several days. Such a delay can cause problems in medical device function, patient treatment, etc.

In certain examples, a target data set is defined to include a unique identifier associated with a data set policy scheduled for delivery of appropriate data set files to selected pump(s) during the data set distribution. A downloaded data set is defined as a unique identifier associated with the data set file downloaded from a data management system, but not programmed on the pump, for example. A programmed data set is defined as a unique identifier associated with the data set file currently being programmed but not in use (e.g., active) by the pump, for example. An active data set is defined as a unique identifier associated with the data set file currently being set and used by the pump, for example.

In certain examples, such as the example medical device management system 100 of FIG. 1, a data management system 110 retrieves and/or generates instructions from a data library 120 to form a data set 125. The data management system 110 begins distributing the data set 125 to one or more target medical devices 130, 135 (e.g., pump(s), apheresis device(s), etc.) according to a specified distribution policy. The data set distribution occurs when a target medical device 130, 135 detects that the target data set 125 is different from its current data set. The medical device 130, 135 can be used while the new data set 125 is distributed from the data management system 110 to the medical device 130, 135.

Figure 2:
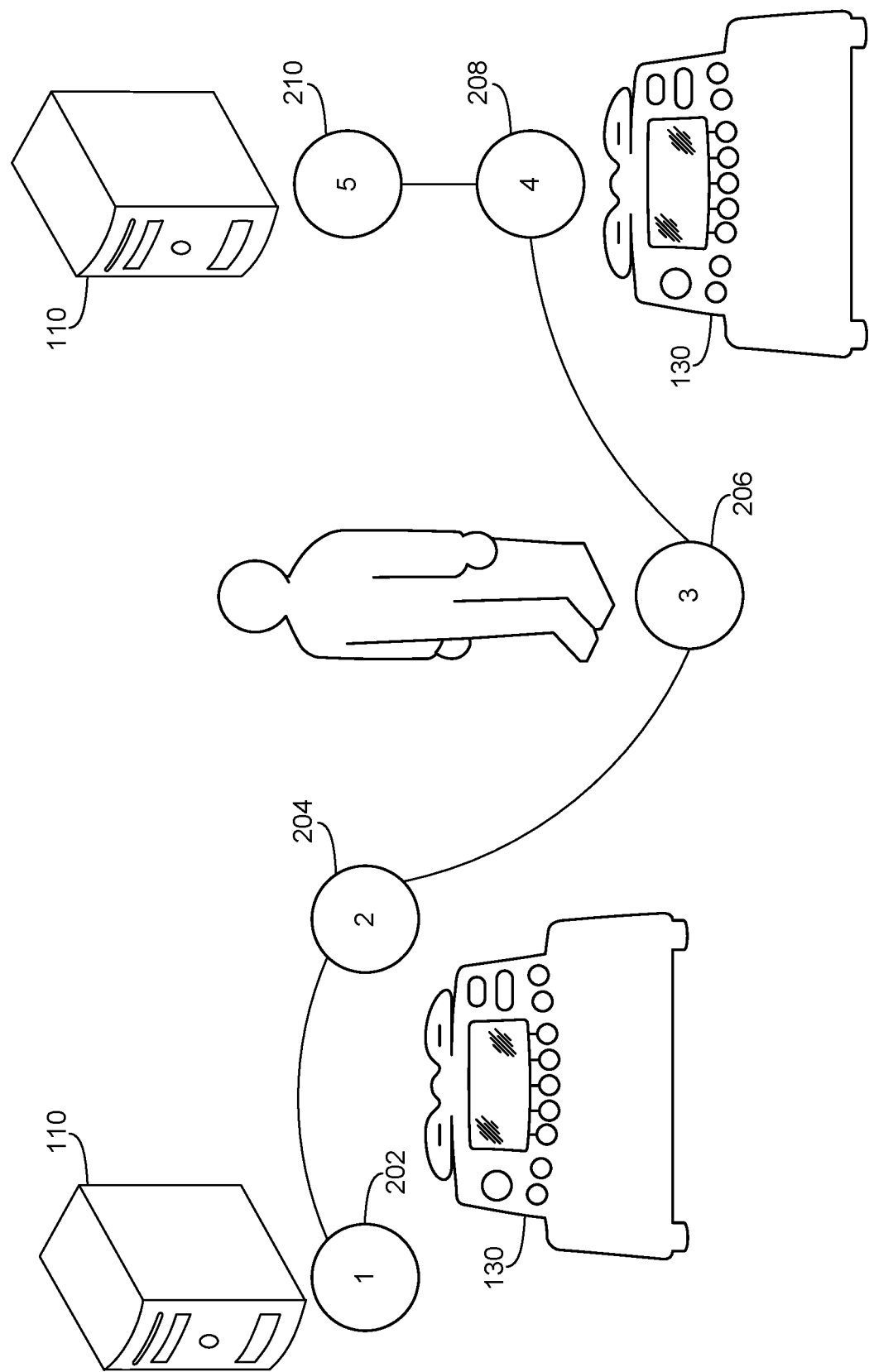
FIG. 2 illustrates an example data set distribution process flow among a plurality of medical devices.

FIG. 2 illustrates an example data set distribution process flow 200 among a plurality of medical devices. At block 202, the data management system 110 maintains a current data set for distribution to a medical device 130. The medical device 130 may be operating at the time (e.g., pump(s) may be infusing, apheresis device(s) may be collecting blood product, etc.)

At block 204, a new data set is distributed to the medical device 130. For example, the medical device 130 periodically checks for a newer version of its data set. If found, the medical device 130 downloads and/or otherwise receives the newer data set and verifies the downloaded data set. The device 130 stores the downloaded data set into non-volatile storage, for example. In certain examples, a user interface of the medical device 130 displays a notification (e.g., an icon, etc.) that the new data set is available to be programmed (e.g., after the pump has finished its current infusion, etc.).

In certain examples, the medical device 130 can be used while the new data set is programmed.

At block 206, a user turns off the medical device 130 (e.g., a nurse turns off the pump). At block 208, the medical device 130 notifies the data management system 110 of its data set upgrade status, and disconnects from the data management system 110 (e.g., from which it has been receiving the data set update). In some examples, the medical device is switched off and on again to activate the newly downloaded data set. In other examples, the downloaded data set is activated upon completion of a current operation of the medical device 130 (e.g., a current infusion, collection, etc., in progress at time of download and/or installation of the data set, etc.).

At block 210, the data management system 110 stores the upgrade status received from the medical device 130. Log information such as transaction time stamp, uptime, success, failure, error, etc., is generated, and a distribution report is generated. The distribution report is sent a user, such as a pharmacist, etc.

Figure 3:
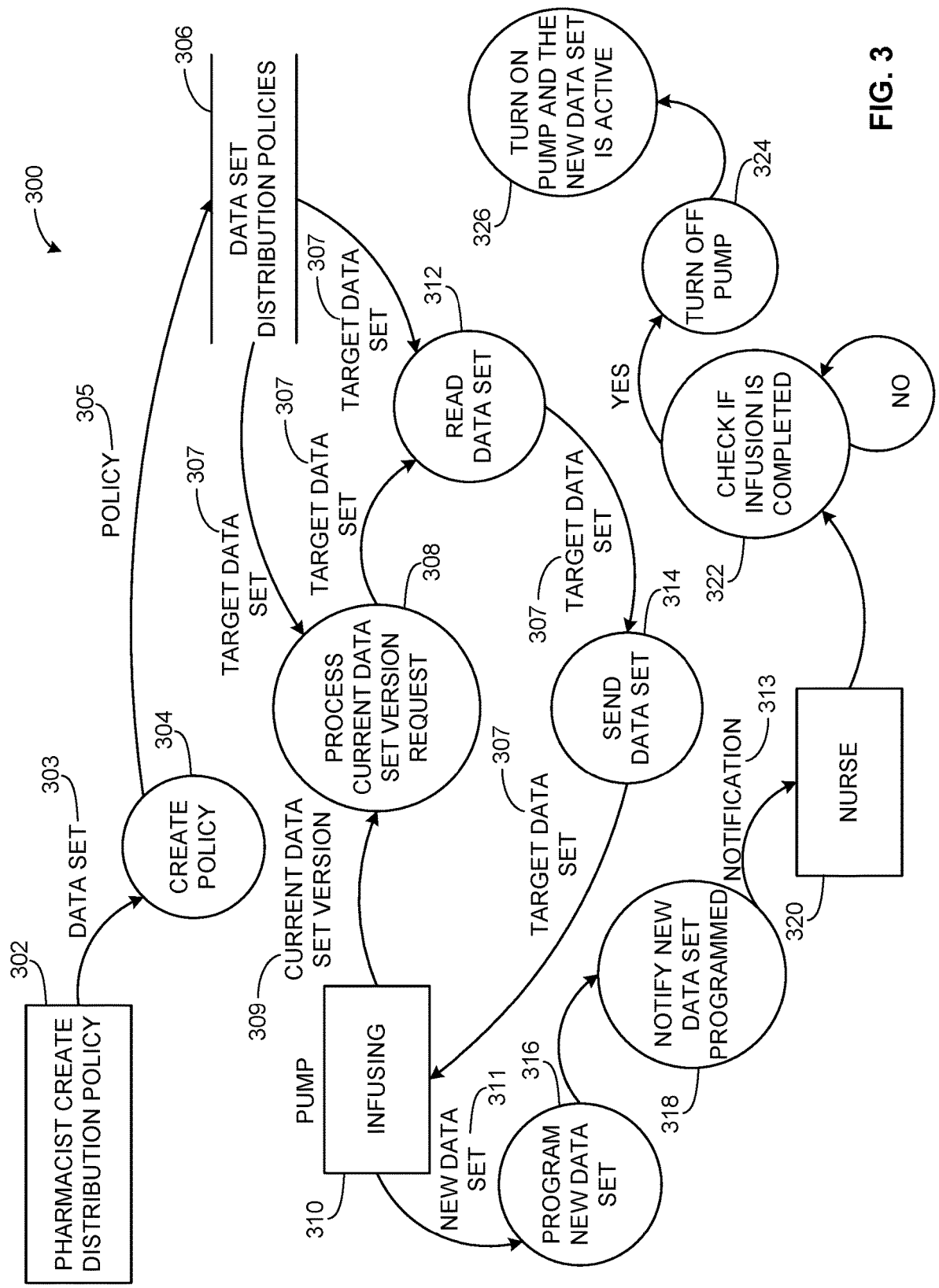
FIG. 3 illustrates an example data flow diagram for data set distribution during infusion by an example infusion pump.

More specifically, FIG. 3 illustrates an example data flow diagram for data set distribution 300 during infusion by an example infusion pump. At block 302, a data set distribution is initiated. For example, a pharmacist can initiate a data set 303 distribution for a medical device, such as an infusion pump, apheresis device, etc., via the data management system 110 (e.g., Fenwal DXT™, etc.). The data set 303 can include a drug library created by a user, retrieved from a library, specified by a pharmaceutical company, etc., that has been uploaded to the data management system 110.

At block 304, a distribution policy is created for the data set 303. For example, the distribution policy can specify where and/or how the data is to be distributed (e.g., to all pumps at all locations, to pumps at a specific location, to specific pump(s), etc.). FIGS. 4A-4I depict example user interfaces for distribution policy creation.

Figure 4A:
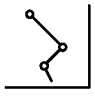
Figure 4B:
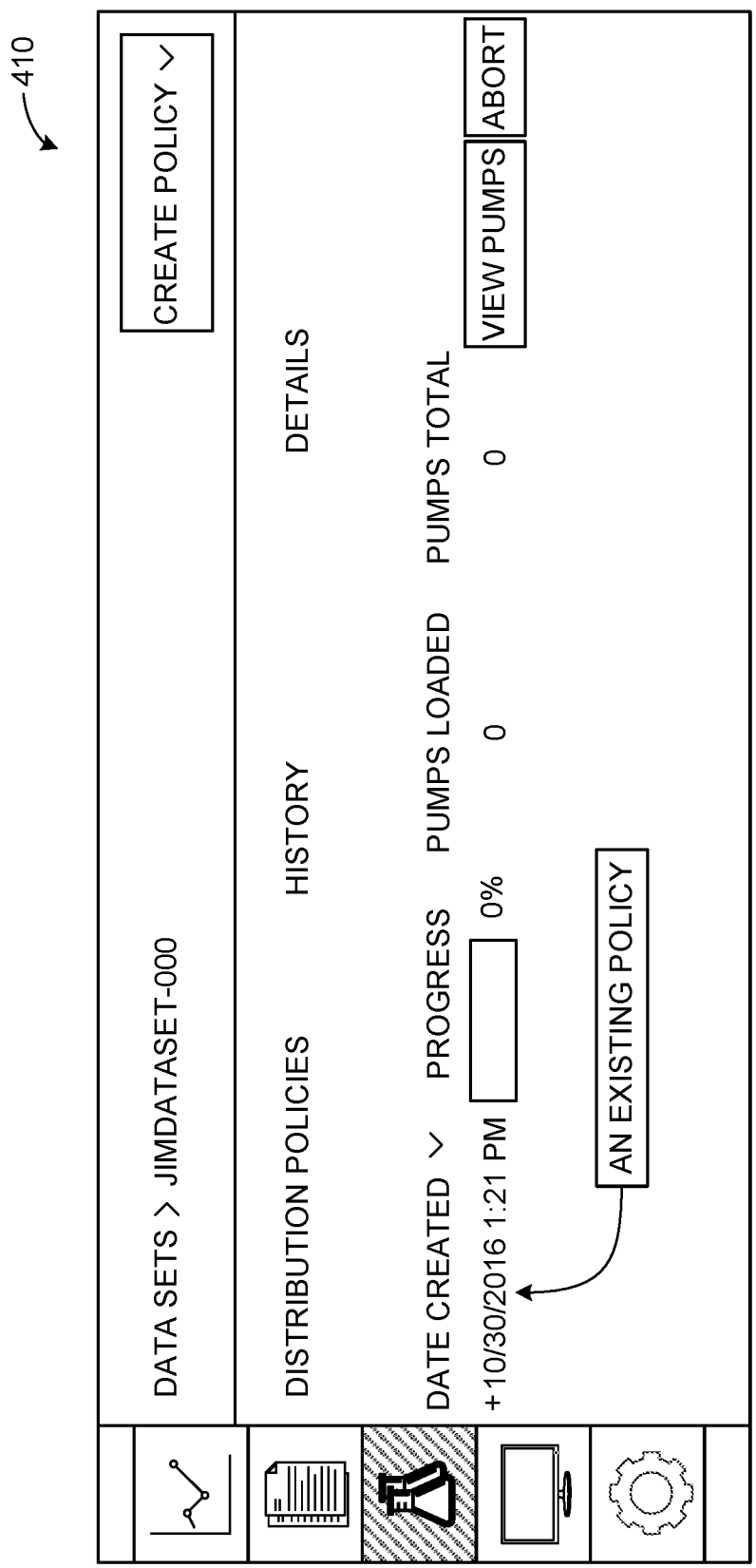
Figure 4C:
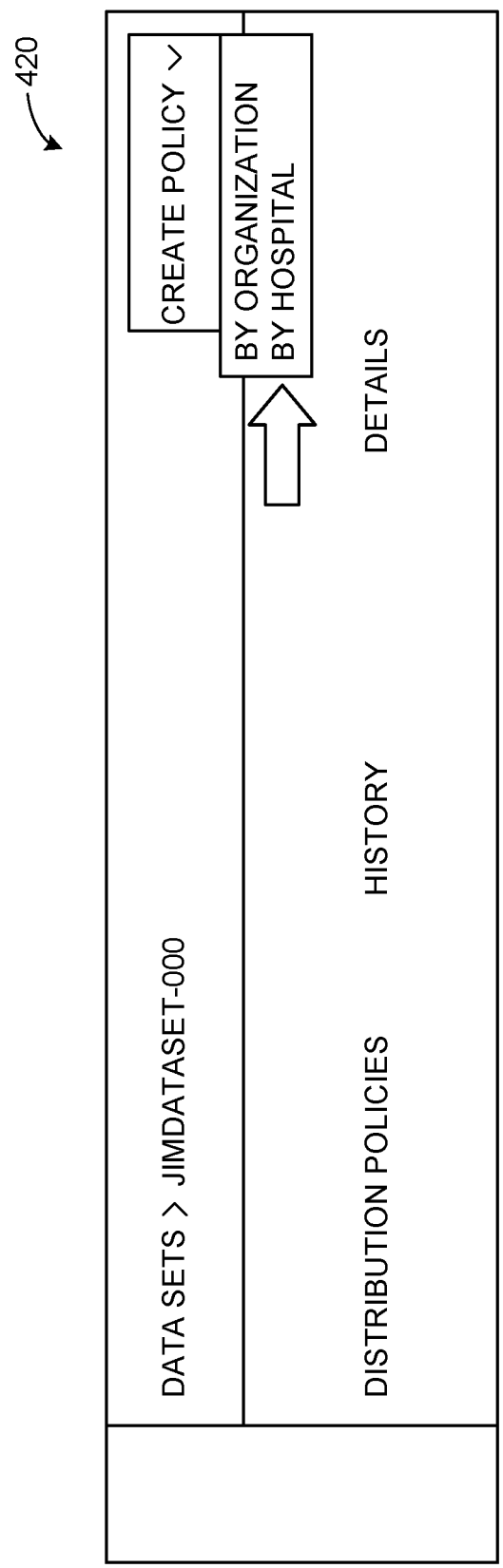
Figure 4D:
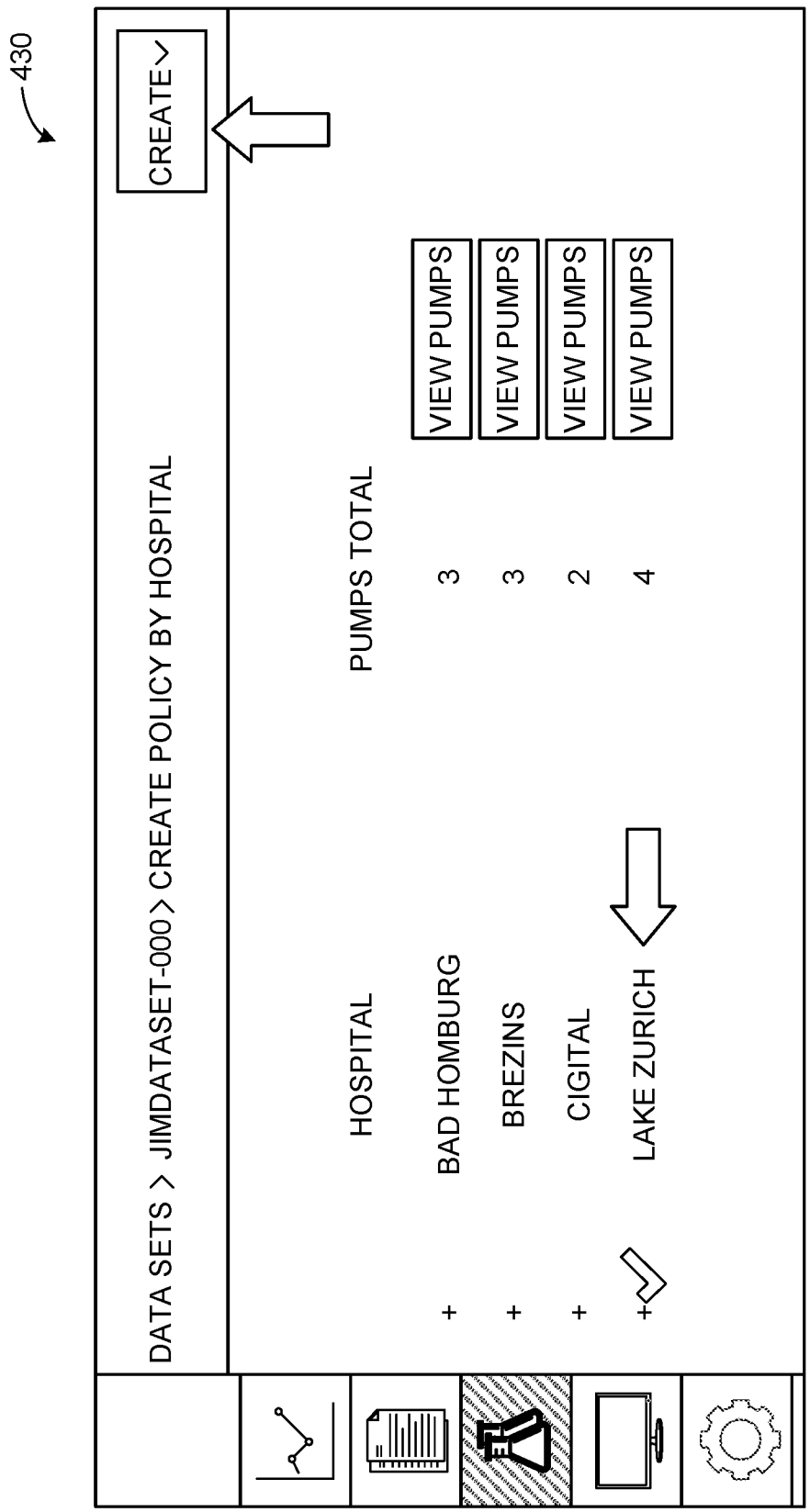
Figure 4F:
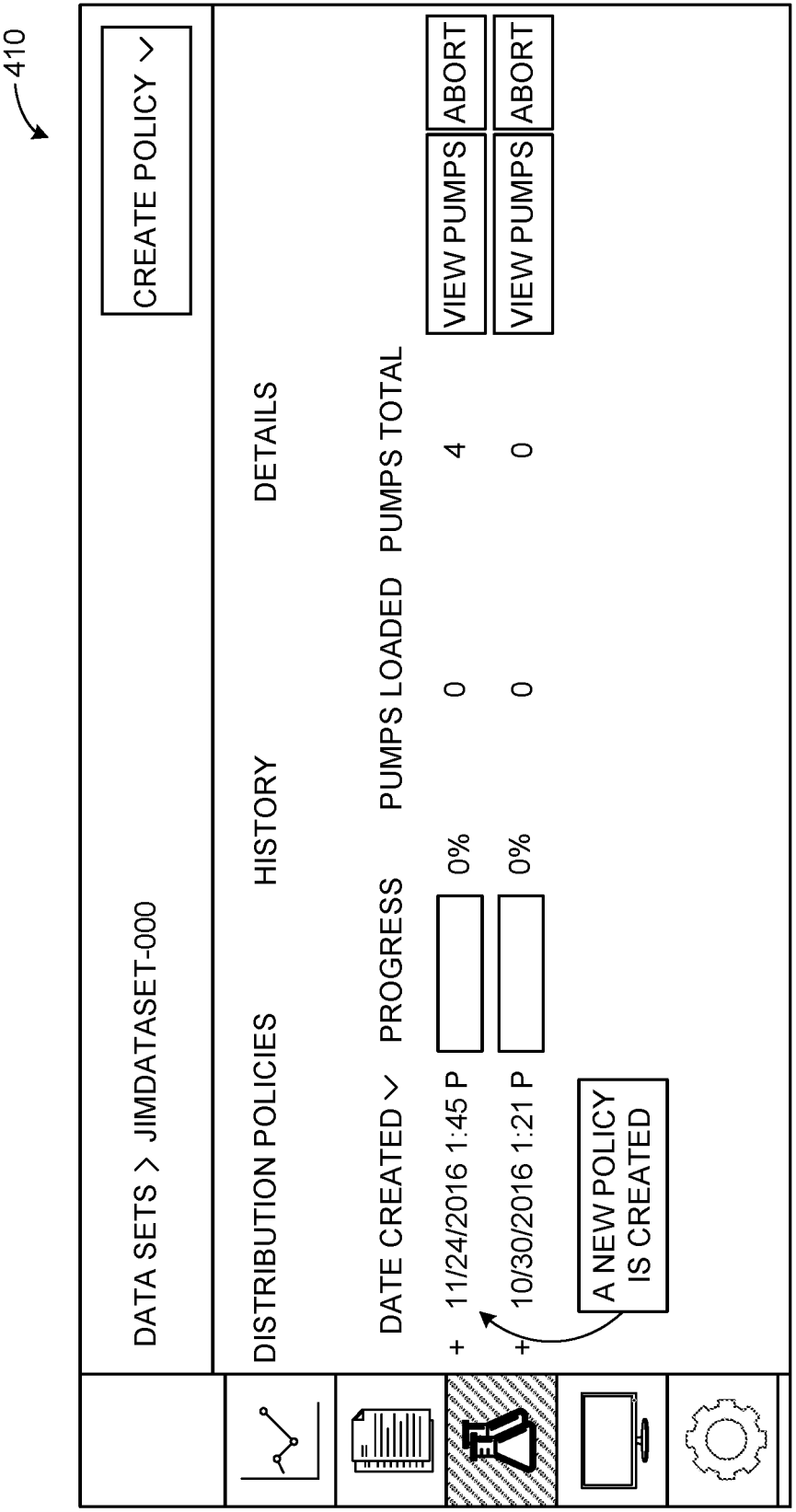

FIG. 4A shows an example data management system user interface 400 from which a user can select a new data set (e.g., JimsDataset-000) from a list of available data sets. An existing distribution policy for the selected data set is shown in the example interface 410 of FIG. 4B. As shown in the example interface 420 of FIG. 4C, selecting "By Hospital" from a Create Policy drop down menu creates a Data Set policy for a particular hospital. Alternatively, a distribution policy can be created for an entire organization. As illustrated in the example of FIG. 4D, one or more hospitals (e.g., the Lake Zurich hospital) can be selected from the interface 430 for distribution of the new data set, and selecting the create button or option generates the appropriate policy 305. The created policy can be reviewed and confirmed via the example interface 440 of FIG. 4E. As illustrated in the updated example interface 410 of FIG. 4F, a new distribution policy has been added to the list with the existing distribution policy.

Figure 4G:
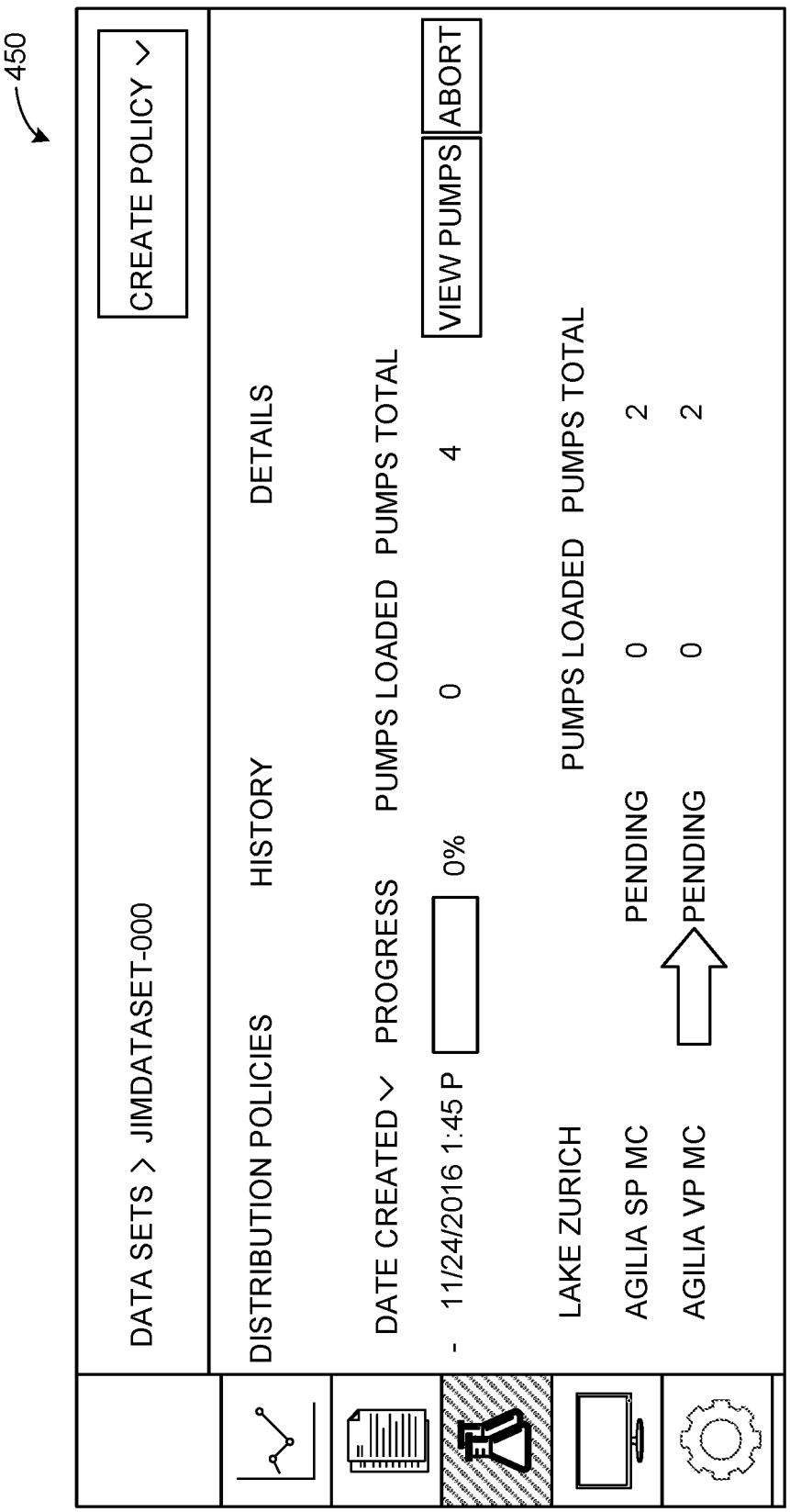
Figure 4H:
Figure 4I:
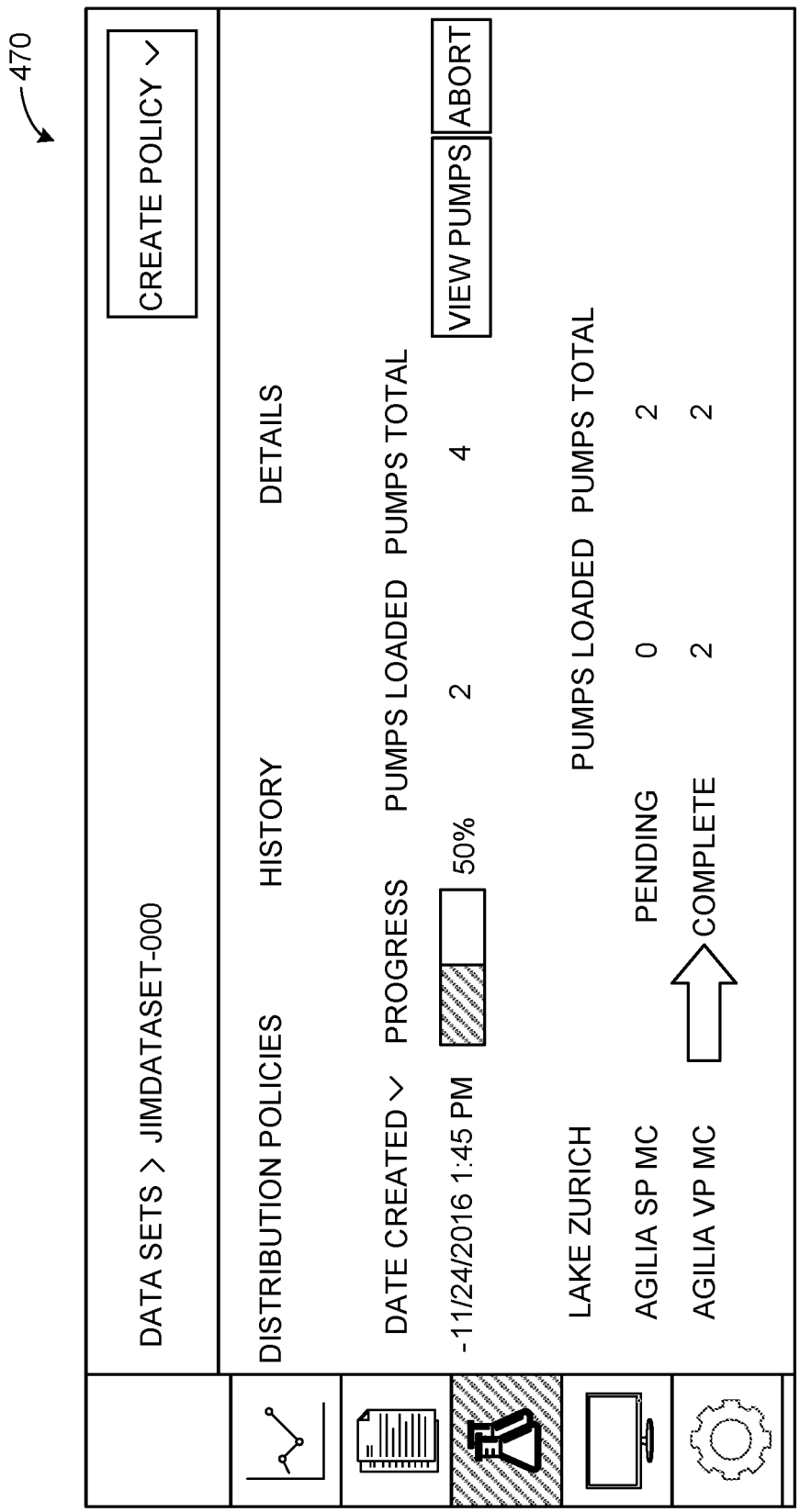

The policy 305 is stored by the data management system with one or more data set distribution policies 306. A target data set 307 is provided according to the policy 305 in the data set distribution policies 306. The example interface 450 of FIG. 4G depicts an example view of which devices (e.g., pumps) are pending distribution of the new data set according to the selected distribution policy 305. As shown in the example view 460 of FIG. 4H, two pumps have downloaded the data set 307 according to the policy 305. As shown in the example view 470 of FIG. 4I, one distribution is complete. Thus, a user can monitor distribution and installation of a data set at one or more medical devices according to a distribution policy via a data management system.

Figure 5A:
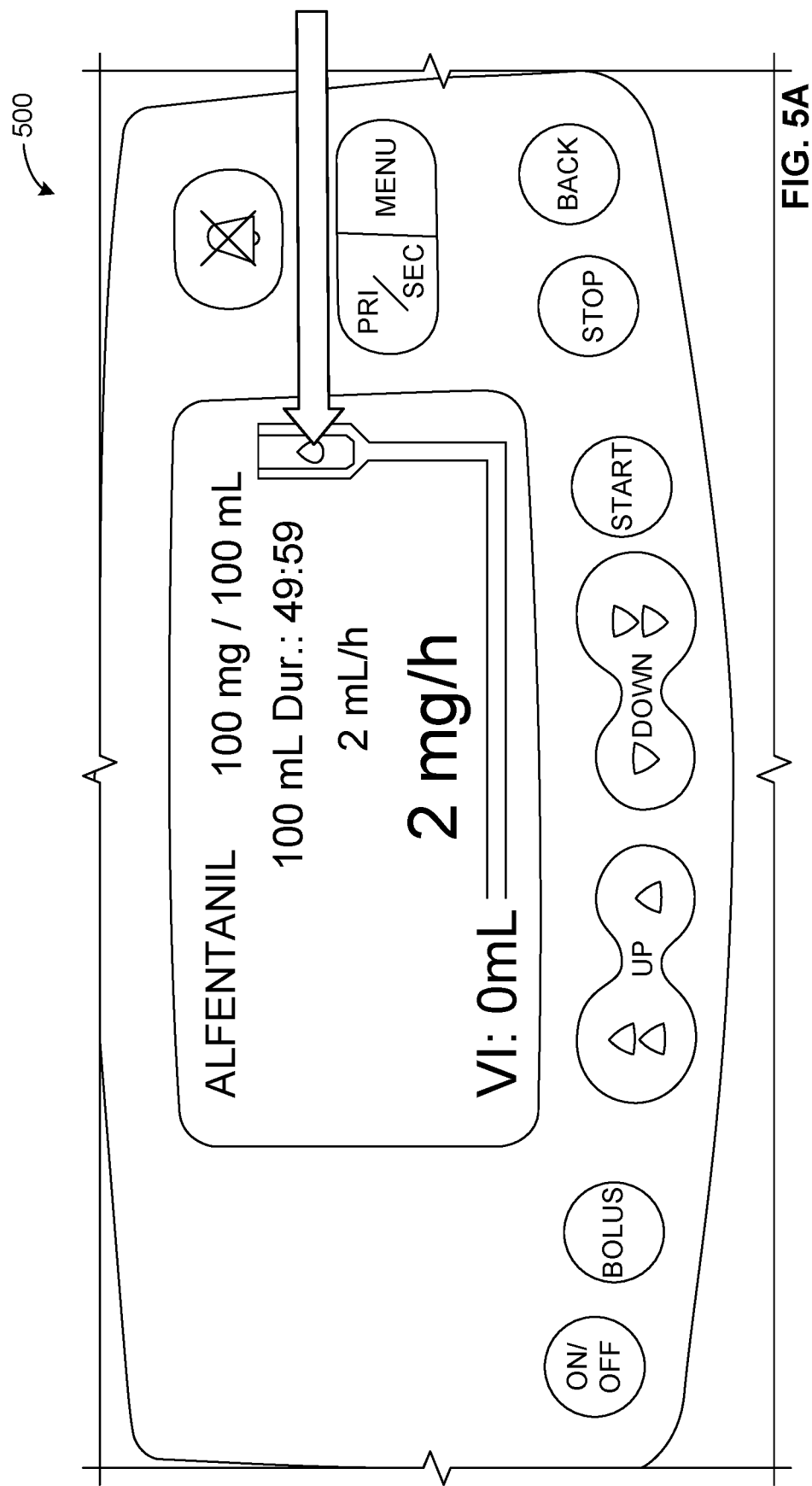
FIGS. 5A-5C depict example medical device interfaces during medical device operation and data set activation.

At block 308, the target data set 307 triggers a request for a current data set version from the medical device 310 (e.g., an infusion pump, apheresis device, etc.). In the example of FIG. 3, the medical device 310 is a pump that is currently infusing a patient. The pump 310 transmits its current data set version 309, which is processed and compared to the target data set 307 (block 308). The target data set 307 is also sent to block 312, which reads the target data set and, at block 314, sends the target data set 307 to the pump 310. FIG. 5A depicts an example user interface 500 for a pump that is infusing and has received the target data set 307 according to the new data set distribution policy 305.

Figure 5B:
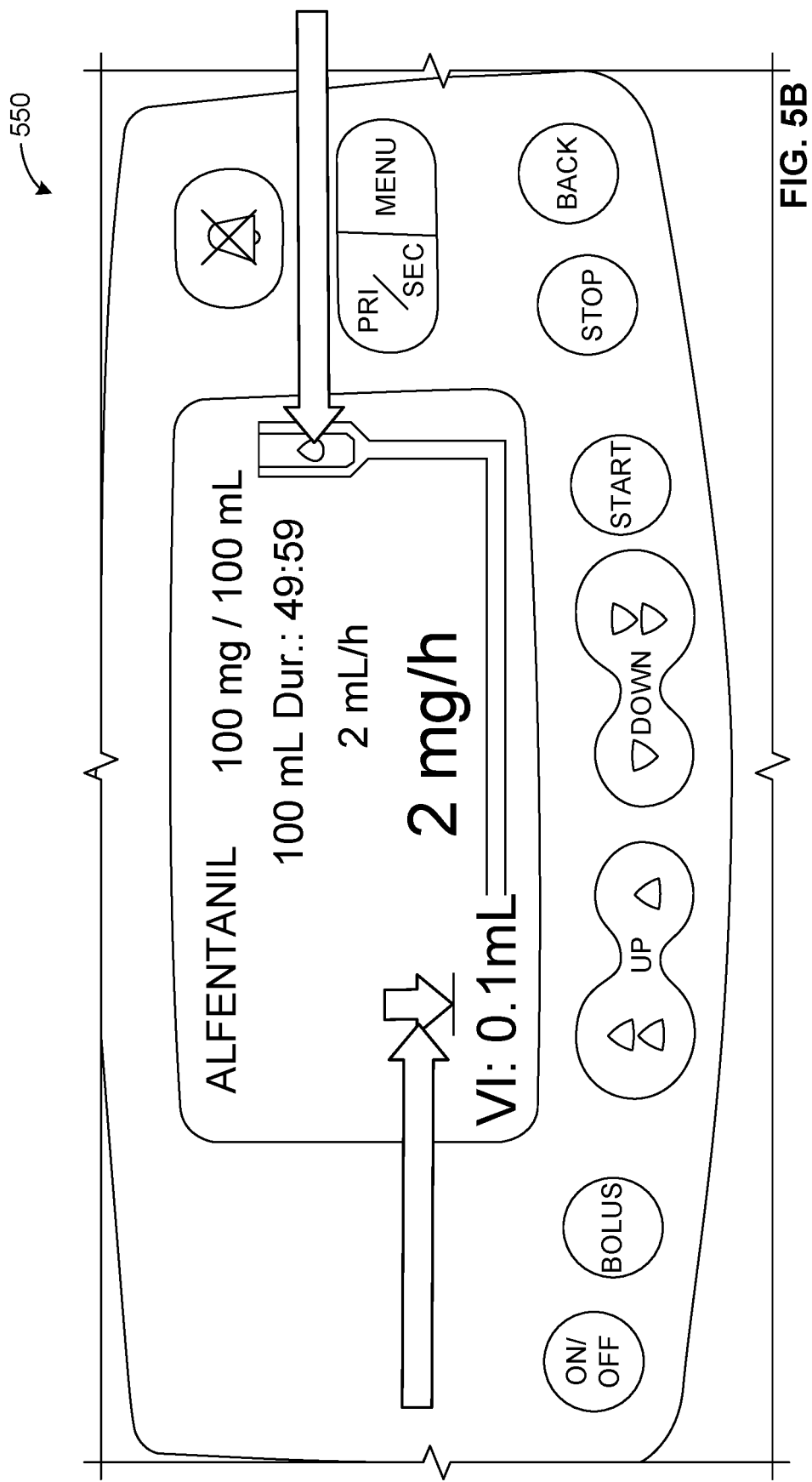

The pump 310 receives the target data set 307 and triggers a configuration with a new data set 311 based on the received target data set 307. In the example of FIG. 3, the pump 310 is infusing when it receives the target data set 307. At block 316, the new data set 311 is programmed with respect to the pump 310 while the pump 310 is infusing. FIG. 5B depicts an example user interface 550 showing that the pump 310 receives and programs the new data set 311 while the pump 310 is infusing.

At block 318, successful programming of the pump 310 with the new data set 311 generates a notification 313. The notification 313 can include an audible (e.g., sound, alarm, etc.), visible (e.g., indicator light, flash, etc.), and/or electronic (e.g., log entry, program trigger, message, etc.) notification 313 of new data set programming. The notification 313 can be provided to an operator, such as a nurse 320, and/or to the data management system 110 and/or other computing device, for example.

Figure 5C:
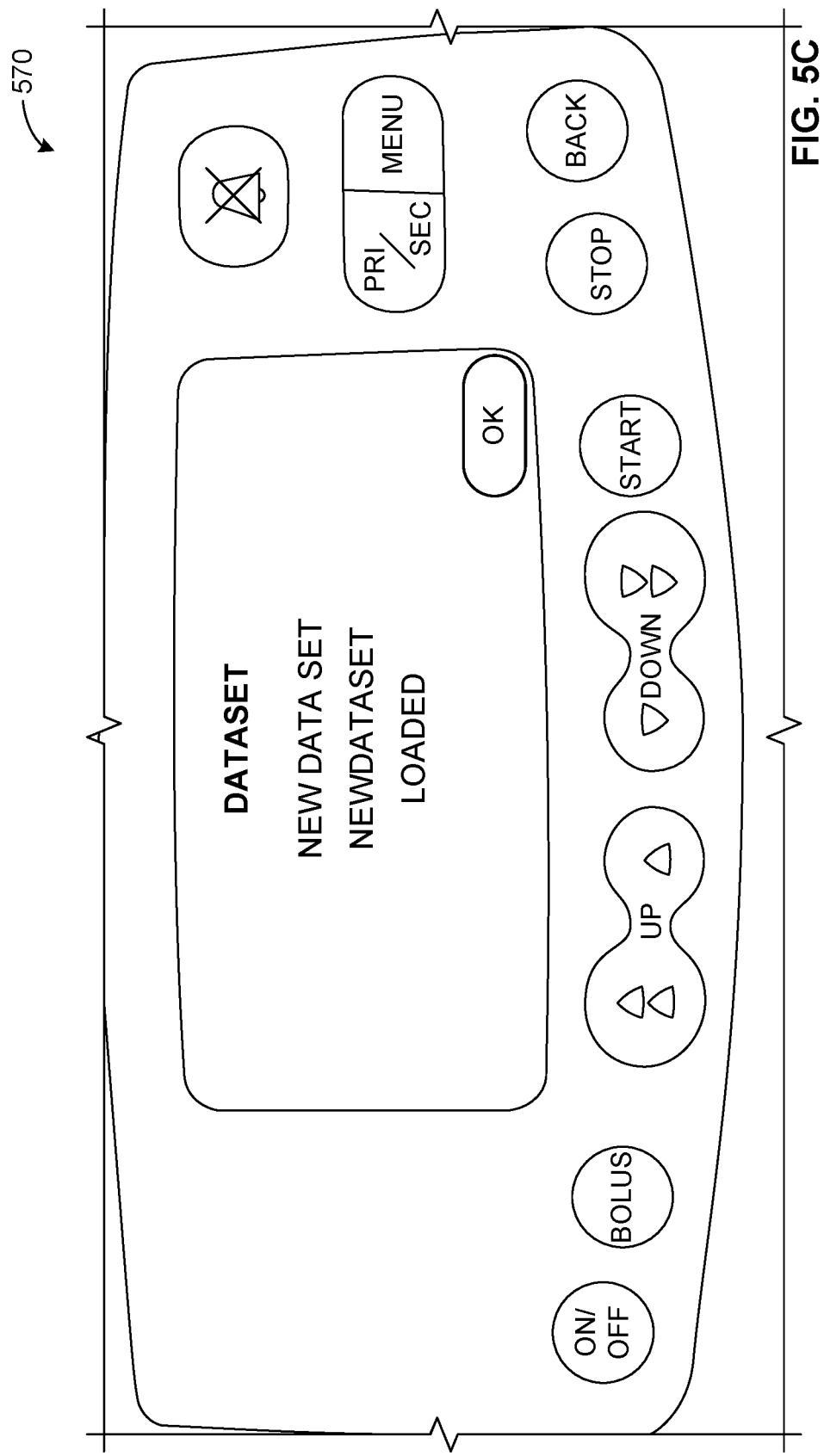

At block 322, the pump 310 is checked to determine if the infusion has been completed. If the pump 310 is still infusing, the pump system 310 waits until the infusion finishes before moving on. If the infusion is complete, then, at block 324, the pump 310 is turned off. The pump 310 can be manually turned off (e.g., by the operator 320) and/or automatically shut down as triggered by the programming of the new data set and infusion completion, for example. At block 326, the pump 310 is turned on to active the new data set at the pump 310. The pump 310 can be manually turned on (e.g., by the operator 320) and/or automatically activated/rebooted according to the new data set. FIG. 5C depicts an example user interface 570 showing a completed infusion with a new data set on the pump 310 following a power off and power on of the pump 310. The example process 300 can be repeated for each of a plurality of medical devices in communication with the data management system 110.

In certain examples, as in block 308, the data management system 110 compares a current version of a pump's data set against a target data set version (e.g., the data set version to be distributed to the pump). The data management system 110 can use an algorithm such as the following example to evaluate data set versions:

| Active (A) | Programmed (P) | Downloaded (D) | Target (T) |
|---|---|---|---|
| 0 | 0 | 0 | 1 |
| 0 | 0 | 1 | IF D != T THEN 1 ELSE 0 |
| 0 | 1 | 0 | IF P != T THEN 1 ELSE 0 |
| 0 | 1 | 1 | IF D != T THEN 1 ELSE 0 |
| 1 | 0 | 0 | IF A != T THEN 1 ELSE 0 |
| 1 | 0 | 1 | IF D != T THEN 1 ELSE 0 |
| 1 | 1 | 0 | IF A != T THEN 1 ELSE 0 |
| 1 | 1 | 1 | IF D != T THEN 1 ELSE 0 |

In the table of rules above, a 1 equals a universally unique identifier (UUID) (e.g., a value representing the data set version), and a 0 equals a UUID with a value of nil or zero (NIL-UUID). According to the above rules, the pump 310 will download the new Data Set from the data management system 110 if the Target is not equal to 0 (e.g., not a NIL-UUID).

Thus, if the pump does not have an active or programmed data set and no data set is downloaded, then the target data set will be downloaded. If the pump does not have an active or programmed data set, and a data set has been downloaded but is not the same version as the target, then the target data set will be downloaded. If the pump has a programmed but not active data set and no data set has been downloaded, the target data set will be downloaded if the programmed data set is not the same version as the target. If the pump does not have an active data set, but it has a programmed and downloaded data set, the target data set will be downloaded if the downloaded data set version is not the same as the target. If the pump has an active data set but none is programmed or downloaded, then the target data set will be downloaded if the active data set is not equal to the target. If the pump has an active data set and one is downloaded, but none is programmed, then the target data set will be downloaded if the downloaded data set is of a different version than the target data set. If the pump has an active data set and a programmed data set but no downloaded data set, then the target data set will be downloaded if the version of the target data set is not equal to the version of the active data set. If the pump has all of an active data set, a programmed data set, and a downloaded data set, then the pump will download the target data set if the target data set version is not equal to the downloaded data set version. Thus, the pump and/or data management system evaluates data set version information based on a UUID representing the version.

In certain examples, such as the table above, a pump can have a currently running (e.g., active) data set, a data set that has been programmed at the pump but not yet activated, and/or a data set that has been downloaded but not yet programmed at the pump. By evaluating whether the target data set is of a different version that the data set(s) currently at the pump, the pump and/or data management system can evaluate whether to download the target data set, which will then be programmed and activated at the pump as described above with respect to FIGS. 2-3.

Figure 6:
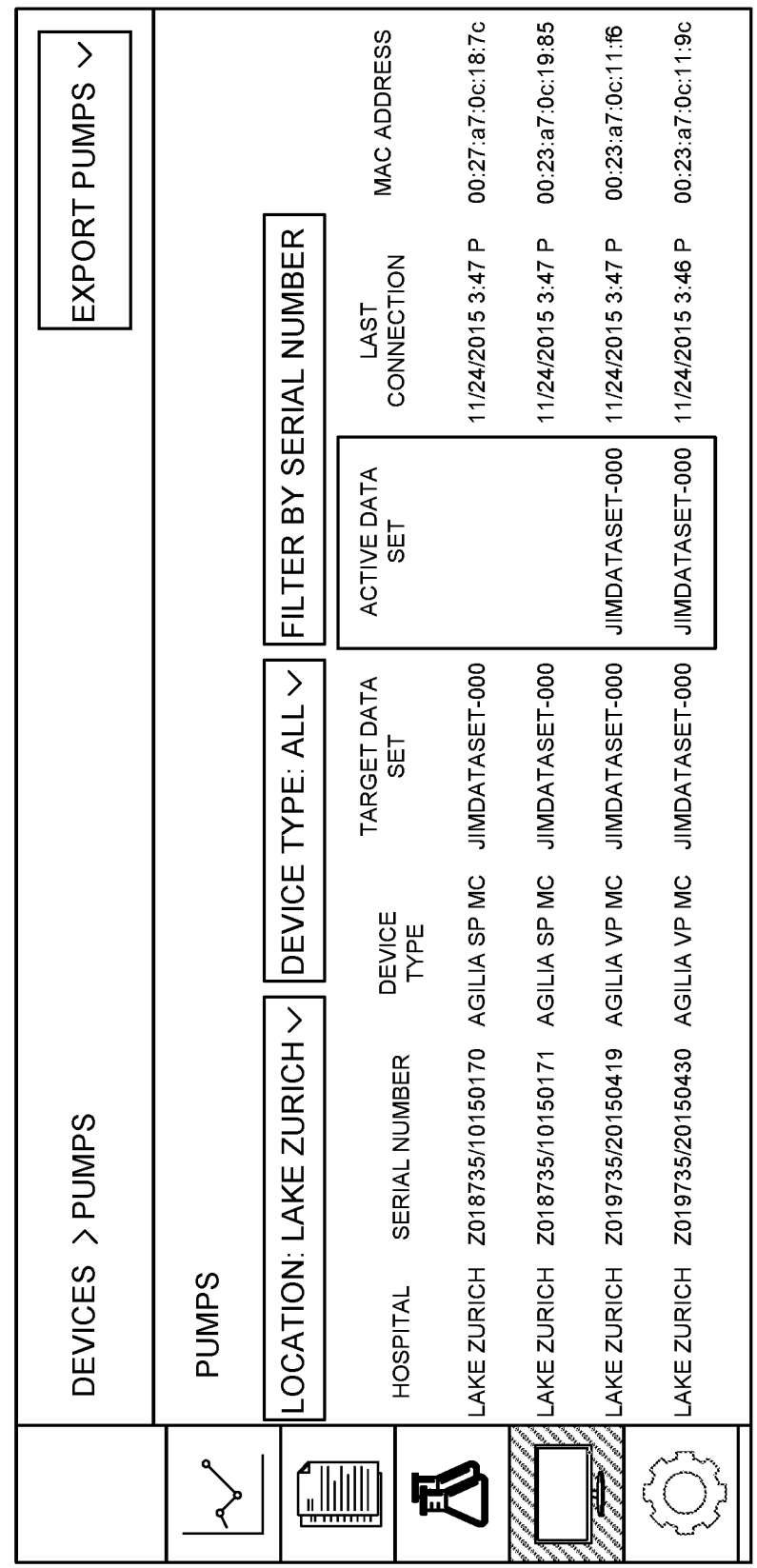
FIG. 6 depicts an example interface displaying a plurality of medical devices and associated data set information.

Thus, certain examples enable distribution of a data set (e.g., drug library and/or other instructions) to a medical device without impacting ongoing device activity. FIG. 6 depicts an example interface 600 displaying a plurality of medical devices (e.g., pumps, etc.) and their associated active data set, target data set, etc., for identification, evaluation, and configuration.

Figure 7:
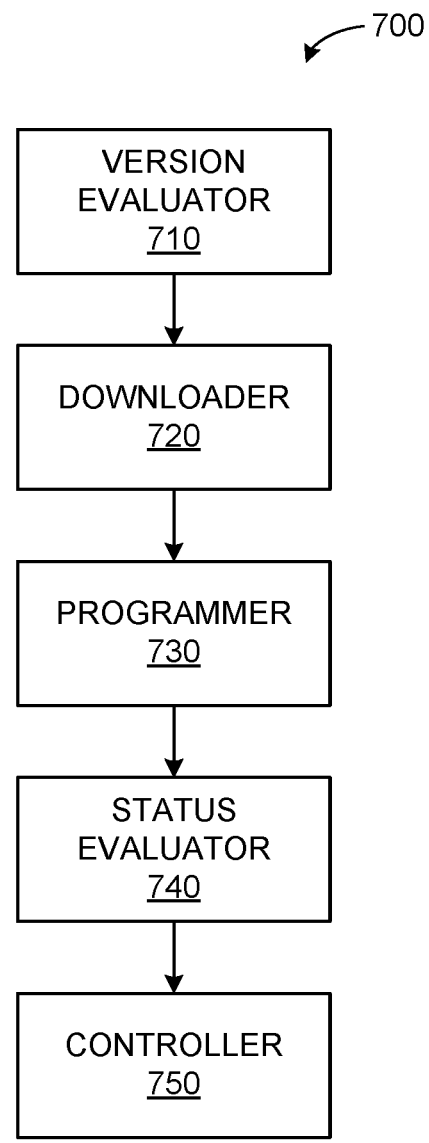
FIG. 7 is a block diagram of an example medical device monitoring and control system.

FIG. 7 illustrates a block diagram of an example medical device monitoring and control system 700. The example medical device control 700 includes a version evaluator 710, a downloader 720, a programmer 730, a status evaluator 740, and a controller 750. The version evaluator 710 receives information regarding a target data set and compares version information for the target data set to version information for one or more data sets residing at the medical device (see, the above described example decision making table and the example process 300 of FIG. 3).

If the version evaluator 710 determines that the target data set is of a different version than a data set currently active, programmed, and/or downloaded to the medical device 700, then the version evaluator triggers the downloader 730 to download the target data set. Once the data set is downloaded by the downloader 720 (e.g., via WiFi™, Bluetooth™, near-field communication (NFC), wired data transfer, etc.), the downloader 720 triggers the programmer 730 to program the medical device with the new data set. In certain examples, the medical device can continue to operate with an active data set while programmed with the new data set. The programmed data set may not become active until power is cycled and/or the medical device is reset, for example.

After the medical device has been programmed with the downloaded data set by the programmer 730, the programmer 730 triggers the status evaluator 740 to evaluate a current operating state of the medical device. If the medical device is currently operating with respect to a patient or other subject (e.g., a blood donor, etc.), then the status evaluator 740 holds status quo until the current operation (e.g., infusion, collection, etc.) of the medical device has been completed. Once the medical device is idle, the status evaluator 740 triggers the controller 750. The controller 750 may prompt and/or otherwise trigger an operator to cycle power at the medical device and/or the controller 750 may, after a defined idle interval, automatically reboot the medical device (e.g., with a prompt and opportunity for user override) to activate the new programmed data set.

Thus, a pump can be infusing a patient with a drug while, in the background, a new drug library is pushed to the pump that will become the new drug library once the current infusion is completed (and power is cycled at the pump). Ongoing operation of the pump is not interrupted, and the new data set is ready for pump operation before the next operation (e.g., next infusion, next collection, etc.). Once a data set distribution policy is identified, created, and/or received, the data management system communicates with the pump control to push information to the medical device as specified in the policy. When the pump is infusing and has received a new drug library, an icon and/or other indicator is displayed on the pump interface (see, e.g., FIG. 5B) to notify a user that the new drug library is available. Nothing is done to affect ongoing operation or jeopardize a current patient, but, once the pump is idle, the user is prompted to cycle power (and/or power is automatically cycled) to active the drug library and associated parameters for pump use.

Figure 8:
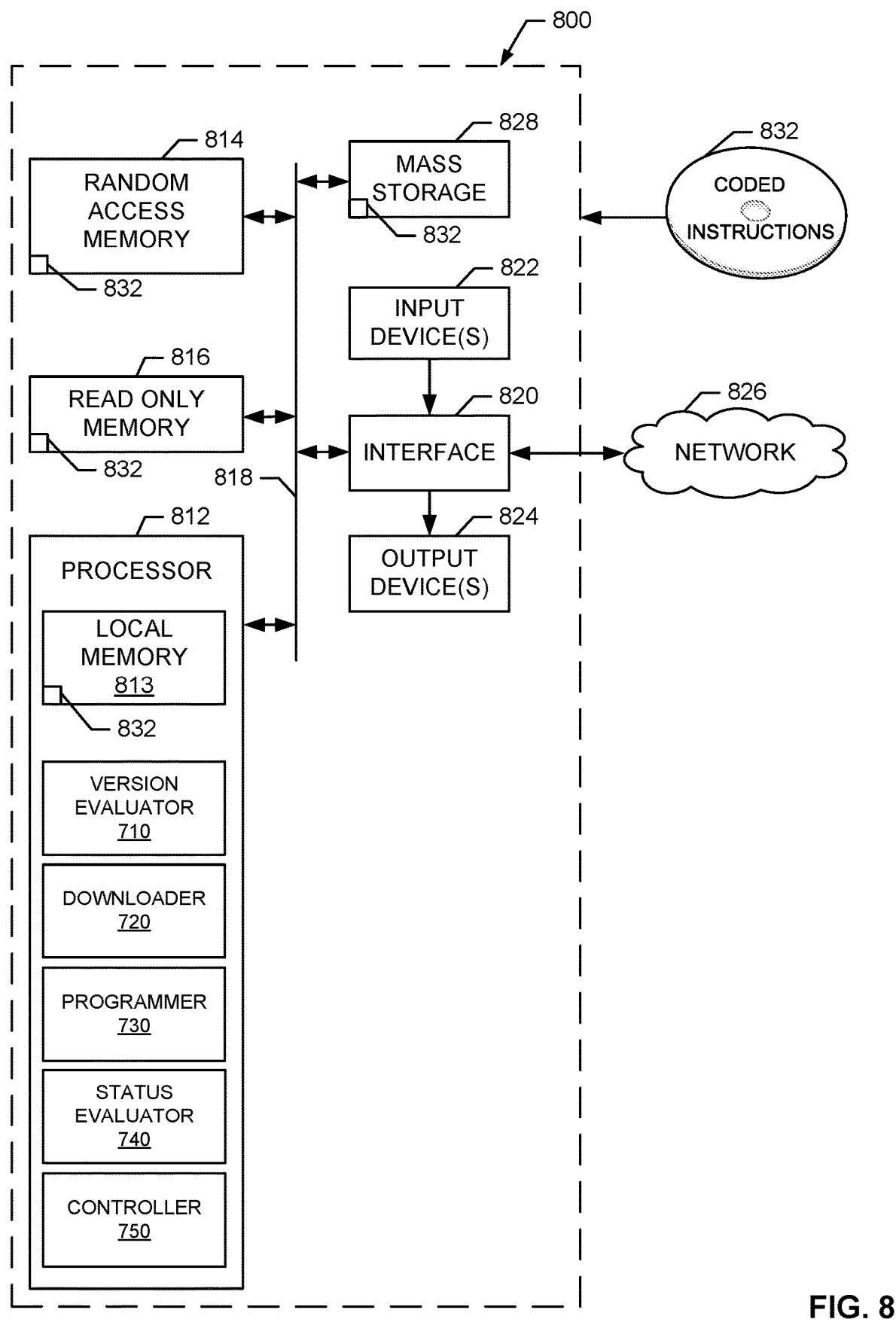
FIG. 8 is a block diagram of an example processor system that can be used to pump, implement, control and/or drive the systems and methods described herein.

FIG. 8 is a block diagram of an example processor platform 800 capable of executing the instructions of FIGS. 2 and 3 to implement the example systems and interfaces of FIGS. 1, 4A-4I, 5A-5C, and 6. The processor platform 800 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer. In the illustrated example, the processor 812 is structured to include the example version evaluator 710, the example downloader 720, the example programmer 730, the example status evaluator 740, and the example controller 750 of the example medical device control system 700.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

Coded instructions 832 representing the flow diagrams of FIGS. 2-3 may be stored in the mass storage device 828, in the volatile memory 814, in the non-volatile memory 816, and/or on a removable tangible computer readable storage medium such as a CD or DVD.

From the foregoing, it will be appreciated that examples have been disclosed which allow drug library and/or other data set(s) to be dynamically provided to and updated at medical devices without affecting operation of the medical device(s) and/or comprising patient safety and/or treatment. By transferring and updating a medical device in the background during device operation, downtime, inefficiency, and inaccuracy can be reduced and/or minimized when the device is rebooted to accept/active changes once the device is again idle after completing a procedure, for example.

Thus, certain examples provide a tracking mechanism to determine what data set is supposed to be loaded on a medical device versus what data set is actually loaded on the medical device. Certain examples provide systems and methods controlled by a policy organized as a data structure that exists as a transaction which provides not only the data itself to read/write but also transitions to certain stages or states (e.g., created, started/distributed, in progress, then switch to completed/aborted, etc.). A life state or stage of the transaction provides a status based on a location covered by the policy.

For example, a system may include infusion pumps at location A and location B, but a policy may only cover location A. Policy A then triggers receipt of status information for only pumps at location A.

Certain examples provide a linkage between a medical device, a location, and a policy. A medical device management system receives a policy and reports status based on the policy. The system knows whether a policy is associated with a particular device/group of devices and determines which device(s) will be updated. The system sends out data and receives status and/or other feedback according to the policy. If the policy does not apply to a device, then that device does not receive the information from the system.

In certain examples, sending of a data file to a device can occur at any time, even if the device is in use (e.g., the pump is infusing). A status or state of the data set is considered to be downloaded. A change or switch in data set to operate the device occurs on power-up, and a new downloaded data set is made effective when the medical device (e.g., infusion pump, etc.) is restarted (e.g., turned off/on). In certain examples, upon restart, the user (e.g., nurse, technician, etc.) has no choice but to acknowledge the new data set or the device will not work. Therefore, the new data policy can be enforced since the user and machine have no choice but to accept the new data set on reboot, for example.

In certain examples, a pharmacy controls the data set and distribution, and the end user (e.g., nurse, technician, etc.) is not given decision-making leeway but must accept the data set to continue using the device. The device management system sends out a data set, and a receiving device is configured to apply the new data set on next reboot. The downloaded data set is held in a download buffer, for example, and, once the device is powered on, the device programs the data set into active memory. The user is then informed of the new data set and instructed to use the device or turn the device off but cannot revert to a prior version of the data set. In certain examples, the device is not forced to reboot for safety reasons (e.g., pumping life-supporting drugs, etc.), so the device and new data set can lag or delay to await a next reset.

Certain examples facilitate automated update of policy over time as the device management system collects data and status from associated medical devices. A third party, such as a pharmacist, provides a new data set and set of target locations based on the collected data. Once the data set has been programmed into a target medical device and the device is powered back on, the new data set/configuration must be accepted or the device is disabled to help prevent a user from using the device in a way that was not intended by the pharmacist, for example.

In certain examples, an initial installation of a data set occurs when a location (e.g., a hospital, clinic, doctor's office, etc.) has not previously used a medical device and/or associated drug library. After installation, updates can occur periodically and/or aperiodically (e.g., update once a week, once a month, on trigger and/or demand, etc.). Updates may occur more frequently at a location that has never used a particular data set (e.g., drug library, etc.) before and less frequently if the location has used a previous version of the data set with the same or different vendor and understands their settings, preferences, etc., for the data set, for example.

Changes can occur based on a variety of reasons such as drug formularies, drug trials, change in limit, etc. (e.g., occurring every 6-12 months, etc.). The pharmacist and/or other data set deliverer can abort the policy, override the policy, etc. A safety-critical change can be implemented as soon as possible, for example.

Thus, certain examples provide an end-to-end system for distribution and monitoring of data sets to medical devices. The medical device management system can determine what data set is being used by each monitored medical device as well as status of new/updated data sets downloaded at the monitored medical device(s). Tracking can facilitate investigation to determine why certain device(s) have not been updated (e.g., hoarded by nurses, not plugged in/battery dead, missing, etc.) to facilitate better resource tracking, troubleshooting, maintenance, and quality control, for example.

Certain examples provide a computer-implemented method for medical device management. The example method includes comparing a first identification of a first data set to a second identification of a second data set at a medical device; when the first identification does not match the second identification, triggering a download of the second data set to the medical device; determining an operating state of the medical device; when the operating state indicates the medical device is idle, triggering activation of the second data set in place of the first data set at the medical device; and facilitating operation of the medical device according to the second data set.

In certain examples, the method further includes programming the medical device with the second data set. In certain examples, the method further includes triggering a notification following the programming of the medical device with the second data set. In certain examples, triggering activation of the second data set includes cycling power at the medical device. In certain examples, the method further includes creating a distribution policy to distribute the second data set to one or more medical devices. In certain examples, the medical device includes a pump. In certain examples, the second data set includes a drug library.

Certain examples provide a tangible computer readable storage medium including program code for execution by a processor. The program code, when executed, is to implement a method for medical device management. The example method includes comparing a first identification of a first data set to a second identification of a second data set at a medical device; when the first identification does not match the second identification, triggering a download of the second data set to the medical device; determining an operating state of the medical device; when the operating state indicates the medical device is idle, triggering activation of the second data set in place of the first data set at the medical device; and facilitating operation of the medical device according to the second data set.

In certain examples, the method further includes programming the medical device with the second data set. In certain examples, the method further includes triggering a notification following the programming of the medical device with the second data set. In certain examples, triggering activation of the second data set includes cycling power at the medical device. In certain examples, the method further includes creating a distribution policy to distribute the second data set to one or more medical devices. In certain examples, the medical device includes a pump. In certain examples, the second data set includes a drug library.

Certain examples provide a system including a processor and a memory particularly configured to implement at least a version evaluator, a downloader, a status evaluator, and a controller. The example version evaluator is configured to compare a first identification of a first data set to a second identification of a second data set at a medical device. The example downloader is configured to, when the first identification does not match the second identification, trigger a download of the second data set to the medical device. The example status evaluator is configured to determine an operating state of the medical device. The example controller is configured to, when the operating state indicates the medical device is idle, trigger activation of the second data set in place of the first data set at the medical device and facilitate operation of the medical device according to the second data set.

In certain examples, the system further includes a programmer configured to program the medical device with the second data set. In certain examples, the programmer is further configured to trigger notification following the programming of the medical device with the second data set. In certain examples, triggering activation of the second data set includes cycling power at the medical device. In certain examples, a distribution policy is created to distribute the second data set to one or more medical devices. In certain examples, the medical device is disabled if the second data set is not activated following the cycling of power at the medical device. In certain examples, the medical device includes a pump, and wherein the second data set includes a drug library.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent. While particular embodiments of the invention have been shown and described, it will be obvious to those skilled in the art that changes and modifications may be made therein without departing from the invention in its broader aspects.

The invention claimed is:

1. A computer-implemented method for medical device management, the method comprising:
   determining data set information associated with a medical device, the data set information including at least two of (a) a first identifier representative of a first version of an active data set at the medical device, (b) a second identifier representative of a second version of a programmed data set at the medical device, or (c) a third identifier representative of a third version of a downloaded data set at the medical device;
   in response to determining that the medical device has the active data set based on the first identifier and the programmed data set based on the second identifier, determining whether the medical device has the downloaded data set based on the third identifier;
   in response to determining that the medical device does not have the downloaded data set based on the third identifier, determining whether the first identifier matches a fourth identifier, the fourth identifier representative of a fourth version of a target data set;
   in response to a determining that the first identifier does not match the fourth identifier, downloading, by the medical device, the target data set from a server to a download buffer of the medical device, the target data set corresponding to executable instructions to facilitate determination of one or more drug delivery parameters by the medical device prior to drug delivery by the medical device;

determining, by the medical device, an operating state of the medical device by:
  in response to determining that the medical device is performing an operation with respect to a subject, determining that the operating state is not idle; and
  in response to determining that the medical device is not performing the operation with respect to the subject, determining that the operating state is idle;
when the operating state indicates the medical device is not idle, preventing, by the medical device, activation of the target data set until the operation is complete by holding the second target data set in the download buffer;
when the operating state indicates the medical device is idle, triggering, by the medical device, activation of the target data set in place of the active data set; and
facilitating, by the medical device, operation of the medical device according to the target data set.

2. The method of claim 1, wherein programming the medical device with the target data set includes:
  turning off the medical device;
  programming the target data set into active memory upon restart of the medical device; and
  disabling the medical device until the target data set is accepted.

3. The method of claim 2, further including triggering a notification following the programming of the medical device with the target data set.

4. The method of claim 1, wherein triggering activation of the target data set includes cycling power at the medical device.

5. The method of claim 1, further including:
  creating a distribution policy to distribute the target data set to one or more medical devices including the medical device;
  displaying, on a first screen of a user interface, a set of the one or more medical devices representative of a type of the one or more medical devices, the type identified by the distribution policy, the user interface separate from the one or more medical devices; and
  displaying, on a second screen of the user interface, a percentage of the set that has activated the target data set.

6. The method of claim 1, wherein the medical device includes a pump, and further including:
  in response to determining that the pump has the downloaded data set based on the third identifier, determining whether the third identifier matches the fourth identifier; and
  in response to determining that the third identifier does not match the fourth identifier, downloading, by the medical device, the target data set from the server to the download buffer of the pump.

7. The method of claim 1, wherein the target data set includes a drug library, and the fourth version is a universally unique identifier representative of a version of the drug library.

8. A tangible computer readable storage medium comprising program code for execution by a processor of a medical device that, when executed, causes the processor of the medical device to at least:
  determine data set information associated with the medical device, the data set information including at least two of (a) a first identifier representative of a first version of an active data set at the medical device, (b) a second identifier representative of a second version of a programmed data set at the medical device, or (c) a third identifier representative of a third version of a downloaded data set at the medical device;
  in response to determining that the medical device has the active data set based on the first identifier and the programmed data set based on the second identifier, determine whether the medical device has the downloaded data set based on the third identifier;
  in response to determining that the medical device does not have the downloaded data set based on the third identifier, determine whether the first identifier matches a fourth identifier, the fourth identifier representative of a fourth version of a target data set;
  in response to a determining that the first identifier does not match the fourth identifier, download the target data set from a server to a download buffer of the medical device, the target data set corresponding to executable instructions to facilitate determination of one or more drug delivery parameters by the medical device prior to drug delivery by the medical device;
  determine an operating state of the medical device by:
    in response to determining that the medical device is performing an operation with respect to a subject, determining that the operating state is not idle; and
    in response to determining that the medical device is not performing the operation with respect to the subject, determining that the operating state is idle;
  when the operating state indicates the medical device is not idle, prevent activation of the target data set until the operation is complete by holding the target data set in the download buffer;
  when the operating state indicates the medical device is idle, triggering activation of the target data set in place of the active data set; and
  facilitating operation of the medical device according to the target data set.

9. The tangible computer readable storage medium of claim 8, wherein the program code, when executed, causes the processor of the medical device to program the medical device with the target data set by:
  turning off the medical device;
  programming the target data set into active memory upon restart of the medical device; and
  disabling the medical device until the target data set is accepted.

10. The tangible computer readable storage medium of claim 9, wherein the program code, when executed, causes the processor of the medical device to trigger a notification following the programming of the medical device with the target data set.

11. The tangible computer readable storage medium of claim 8, wherein the program code, when executed, causes the processor of the medical device to trigger activation of the target data set by cycling power at the medical device.

12. The tangible computer readable storage medium of claim 8, wherein the program code, when executed, causes the processor of the medical device to obtain the target data set based on a distribution policy corresponding to the server distributing the target data set to one or more medical devices including the medical device.

13. The tangible computer readable storage medium of claim 8, wherein the medical device includes a pump and the program code, when executed, causes the processor of the pump to:
  in response to determining that the pump has the downloaded data set based on the third identifier, determine whether the third identifier matches the fourth identifier; and in response to determining that the third identifier does not match the fourth identifier, download the target data set from the server to the download buffer of the pump.

14. The tangible computer readable storage medium of claim 8, wherein the target data set includes a drug library, and the fourth version is a universally unique identifier representative of a version of the drug library.

15. A system comprising:
a processor of a medical device; and
a memory including instructions that, when executed, cause the processor of the medical device to:
   determine data set information associated with the medical device, the data set information including at least two of (a) a first identifier representative of a first version of an active data set at the medical device, (b) a second identifier representative of a second version of a programmed data set at the medical device, or (c) a third identifier representative of a third version of a downloaded data set at the medical device;
   in response to determining that the medical device has the active data set based on the first identifier and the programmed data set based on the second identifier, determine whether the medical device has the downloaded data set based on the third identifier;
   in response to determining that the medical device does not have the downloaded data set based on the third identifier, determine whether the first identifier matches a fourth identifier, the fourth identifier representative of a fourth version of a target data set,
   in response to determining that the first identifier does not match the fourth identifier, download the target data set from a server to a download buffer of the medical device, the target data set corresponding to executable instructions to facilitate determination of one or more drug delivery parameters by the medical device prior to drug delivery by the medical device;
   determine an operating state of the medical device by:
      in response to determining that the medical device is performing an operation with respect to a subject, determining that the operating state is not idle; and
      in response to determining that the medical device is not performing the operation with respect to the subject, determining that the operating state is idle;
   when the operating state indicates the medical device is not idle, prevent activation of the target data set until the operation is complete by holding the target data set in the download buffer;
   when the operating state indicates the medical device is idle, trigger activation of the target data set in place of the active data set; and
   facilitate operation of the medical device according to the target data set.

16. The system of claim 15, wherein the processor of the medical device is to program the medical device with the target data set by:
   turning off the medical device;
   programming the target data set into active memory upon restart of the medical device; and
   disabling the medical device until the target data set is accepted.

17. The system of claim 16, wherein the processor of the medical device is to trigger a notification following the programming of the medical device with the target data set.

18. The system of claim 15, wherein the processor of the medical device is to trigger activation of the target data set by cycling power at the medical device.

19. The system of claim 15, wherein the processor of the medical device is to disable the medical device when the target data set is not activated following the cycling of power at the medical device.

20. The system of claim 15, wherein the medical device includes a pump, the target data set includes a drug library, the fourth version is a universally unique identifier representative of a version of the drug library, and the processor of the medical device is to:
   in response to determining that the pump has the downloaded data set based on the third identifier, determine whether the third identifier matches the fourth identifier; and
   in response to determining that the third identifier does not match the fourth identifier, download the target data set from the server to the download buffer of the pump.

* * * * *

UNITED STATES PATENT AND TRADEMARK OFFICE
CERTIFICATE OF CORRECTION

PATENT NO. : 10,740,436 B2  
APPLICATION NO. : 15/359680  
DATED : August 11, 2020  
INVENTOR(S) : Witold Moskal and Maciej Wroblewski Page 1 of 1

It is certified that error appears in the above-identified patent and that said Letters Patent is hereby corrected as shown below:

In the Claims

Column 12, Line 60 (Claim 1):  
Replace "response to a determining" with -- response to determining --.

Column 13, Line 12 (Claim 1):  
Replace "holding the second target" with -- holding the target --.

Column 14, Line 13 (Claim 8):  
Replace "response to a determining" with -- response to determining --.

Signed and Sealed this  
Twenty-fourth Day of November, 2020

Andrei Iancu  
*Director of the United States Patent and Trademark Office*